United States Patent
Gapes et al.

(10) Patent No.: US 7,247,739 B2
(45) Date of Patent: Jul. 24, 2007

(54) TRANSESTERIFICATION AND ESTERIFICATION OF FATTY ACIDS AND TRIGLYCERIDES BY DISPERSION AND DISPERSION METHOD FOR THE PRODUCTION OF FATTY ACID METHYLESTERS

(76) Inventors: Richard Gapes, Mariensteig 15/2/4, Vienna (AT) A-1133; Hans Baumgartner, Rudolf Nurejev Promenade 9-21, Vienna (AT) A-1220

( * ) Notice: Subject to any disclaimer, the term of this patent is extended or adjusted under 35 U.S.C. 154(b) by 0 days.

(21) Appl. No.: 10/525,353

(22) PCT Filed: Aug. 25, 2003

(86) PCT No.: PCT/AT03/00242

§ 371 (c)(1),
(2), (4) Date: Sep. 14, 2005

(87) PCT Pub. No.: WO2004/018405

PCT Pub. Date: Mar. 4, 2004

(65) Prior Publication Data

US 2006/0111579 A1    May 25, 2006

(30) Foreign Application Priority Data

Aug. 23, 2002   (AT)   ............................. A 1262/2002

(51) Int. Cl.
    *C07C 51/43*   (2006.01)
(52) U.S. Cl. ...................................................... 554/174
(58) Field of Classification Search ................. 554/174
    See application file for complete search history.

(56) References Cited

U.S. PATENT DOCUMENTS

| 2,360,844 A | 10/1944 | Bradshaw |
| 2,383,632 A | 8/1945 | Trent |
| 4,668,439 A | 5/1987 | Billenstein et al. |
| 2002/0013486 A1* | 1/2002 | Ergun et al. ................. 554/174 |

FOREIGN PATENT DOCUMENTS

| DE | 196 38 460 | 3/1998 |
| DE | 199 08 978 | 9/2000 |
| DE | 100 43 644 | 3/2002 |
| EP | 0 249 463 A2 | 12/1987 |
| WO | WO 99/26913 | 6/1999 |

* cited by examiner

*Primary Examiner*—J. Parsa

(57) ABSTRACT

The invention relates to a method for the basic or acidic catalyzed esterification and transesterification of fatty acids, such as oils and fats, i.e. the esters of glycerin with fatty acids, by dispersion of low alcohols, especially methyl alcohol, in the liquidic initial product. The invention is characterized in that the methyl alcohol (or other low alcohols) is fully dispersed in the reaction mixture. The invention also relates to embodiments of said method.

14 Claims, 3 Drawing Sheets

TRANSESTERIFICATION AND ESTERIFICATION OF FATTY ACIDS AND TRIGLYCERIDES BY DISPERSION AND DISPERSION METHOD FOR THE PRODUCTION OF FATTY ACID METHYLESTERS

TECHNICAL FIELD

The invention concerns a process for carrying out the basic or acidic catalyzed acid-esterification and trans-esterification of oils and fats, i.e. the esters of glycerin with fatty acids and also the fatty acids themselves, by introducing methyl alcohol or other short chain alcohols into the liquid raw material.

BACKGROUND

For many applications it is desirable to modify fats using trans-esterification for various technical requirements, in particular when the production of motor fuels from biological sources is required.

There are known processes of this type for the trans-esterification of various vegetable oils and fats which form a multistage process, which is non-continuous and carried out in stages, finally resulting in glycerin, water and the desired methyl esters of the fatty acids, which initially formed an ester with the glycerin. It is also possible to use a different short chain alcohol, for example ethanol, propanol, butanol and in some cases even pentanol, to form the corresponding esters instead of the methyl alcohol. However, methyl alcohol is usually used for economic reasons and due to the simplicity of the reaction. As the length of the chain increases, the acid catalysis becomes more efficient and as such becomes a serious alternative. Impurities in the raw material should be removed to the extent that they do not cause any problems in the process. Prior cleaning of the oil reduces the disadvantages caused by impurities: side reactions, an increased use of chemicals, a slower conversion, etc.

On the other hand, problems are caused by the slow process, which involves treatment of the raw oils with methyl alcohol, usually catalyzed in a large volume mixing vessel for periods usually measured in hours. This reaction stage is followed by a separation stage which in turn takes place in a large settling vessel where any glycerin present collects at the bottom and the intermediate product, which has been up to 90% or more converted, floats although sometimes only after several hours of separation.

The floating intermediate product is once again introduced into a reaction vessel and again transformed using methyl alcohol and alkali, whereby a transformation of about 99% or more of the raw material is reached after several hours.

This product also has to be decanted which also takes place in a large separation vessel where the product floats and is finally drawn off. It is this product which finally undergoes final product purification.

The acid esterification of the fatty acids takes place analogous to the trans-esterification described above, except that the reaction takes place more slowly and water is produced as a side product instead of glycerin. The reaction is normally catalyzed with acid. The invention relates equally to the acid esterification and the trans-esterification of fatty acids and oils or of fats in mixtures with each other as well as with other components.

In summary, it is clear that the current most commercially used processes work in the manner described above. In principle, all these processes are based on early developments which were developed for the production of fatty acid methylesters as raw materials for the chemical industry (U.S. Pat. Nos. 2,360,844, 2,383,632).

The invention is characterized by the fact that (a) technically clean short chain alcohol(s) is/are dispersed into the oil(s) or fat(s) present as a liquid raw material and perhaps contaminated with free fatty acids in the presence of a basic or acidic catalyst. In other words, the invention concerns processes for the basic or acid catalyzed acid esterification and/or trans-esterification of fatty acids and/or oils and/or fats, that is the esters of glycerin with fatty acids, through introduction of short chain alcohols. In particular, methyl alcohol, is introduced into the liquid raw material. Further the process uses commercially pure short chain alcohol(s) dispersed into oil(s) or fat(s) present as a liquid raw material and perhaps contaminated with free fatty acids in the presence of a basic or acid catalyst. In one example, methyl alcohol is used as the alcohol and is completely dispersed in the reaction mixture. The dispersion can have a globule size (diameter) of about 1 µm, and preferably about 5 µm. Indeed, the dispersion can have a globule size of less than 50 µm, and preferably under 15 µm. In another aspect, the dispersion is produced using a dispersion machine, in particular a multi-stage high power dispersion machine.

In the case of the invented process, the dispersion is produced with normal dispersion equipment. This equipment is designed to produce a temporarily stable dispersion. It was often assumed that the mixture created in the dispersion equipment separates only very slowly and because of that the separation times for the glycerin phase were very long. It could be demonstrated, however, that a very rapid phase separation occurs through selection of the correct dispersion equipment.

BRIEF DESCRIPTION OF THE DRAWINGS

The invention will be described in more detail below by way of a detailed description of the current State of the Technique and reference to diagrams whereby.

DETAILED DESCRIPTION

The choice of globule size is important when applying the invention. FIG. 1 to 5 (source: manufacturer's information) show the distribution of globule size when using different equipment from the same type of machine. An important characteristic of the dispersion equipment is that the globule size and its spectrum remain independent of the flow-rate up to its maximum capacity. This fact is of particular importance below in relation to the patent WO 99/26913 A1.

Figure 3:
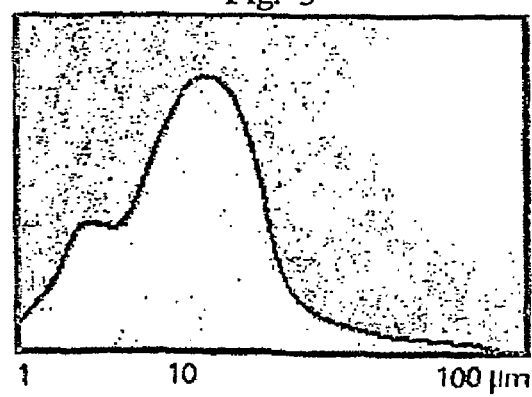
Figure 4:
Figure 5:

The equipment suitable for the acid esterification and trans-estenfication can be determined simply in a series of experiments. The dispersion should preferably comprise of globule sizes (diameters) above 1 µm, preferably above 5 µm, and below 50 µm., preferably below 15 µm. Distributions as shown in FIG. 3 and 4 are particularly advantageous.

Figure 6:
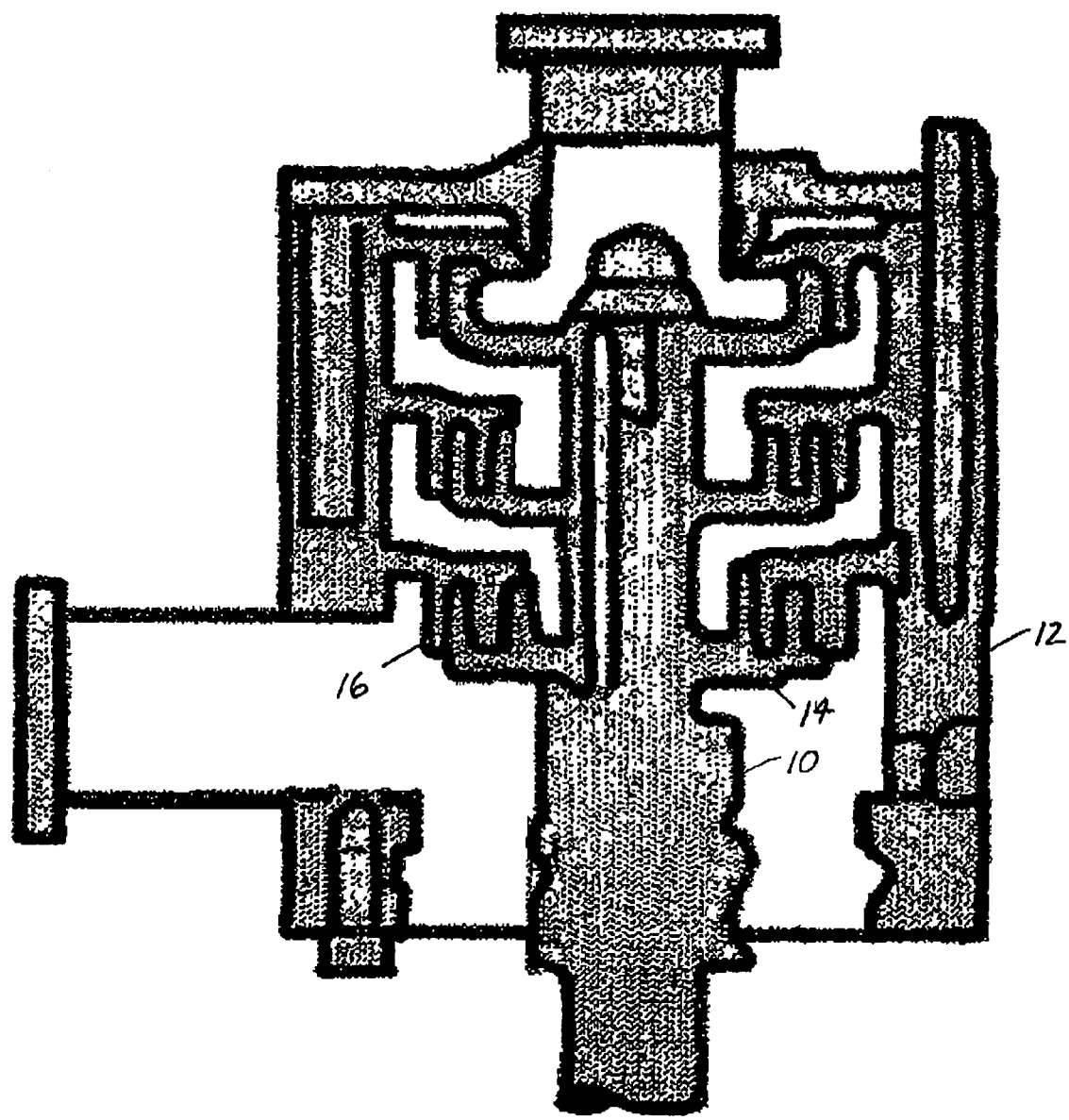
FIG. 6 shows dispersion equipment suited to the invention.

FIG. 6 shows the basic construction of dispersion equipment. FIG. 6 shows the rotor 10 and stator 12 for an apparatus suitable for performing the process according to the present invention. In FIG. 6, the rotor 10 is mounted vertically inside the casing/stator 12. Attachments 14 on the rotor are arranged to fit with attachments 16 on the stator and serve to create strong turbulence when rotating. When this construction is compared with the equipment described in WO 99/26913 A1, De 199 08 978 A1, EP 0 249 463 A2, U.S. Pat. No. 4,668,439 A, DE 196 38 460 A1 and DE 100 43 644 A1 then the difference is easily recognizable. In the documents mentioned above, either a static mixer (or a derivative) or a normal mixing vessel are used.

A further particular characteristic of the invention, distinguishing it from the patents mentioned above, is the fact that several of them involve a several stage process, whereas the product is available in satisfactory quality (according to the current EN) after just one stage if the invented dispersion process is used.

A further important difference from WO 99/26913 A1 is that the dispersion equipment operates at normal atmospheric pressure (assuming no other process engineering requirements specify otherwise). A positive pressure as described in WO 99/26913 A1 is not necessary.

Having described the general differences between the invented process and the documents WO 99/26913 A1, DE 199 08 978 A1, U.S. Pat. No. 4,668,439 A, DE 196 38 460 A1, DE 100 43 644 A1, each of the differences or improvements which the submitted process brings will now be described. Firstly, however, the difference between dispersion and emulsion will be described. Dispersion involves increasing the phase boundary area between two insoluble liquids. If this process results from the addition of surface active substances then the term emulsion is used and usually very different characteristics apply (refer: Marko Zlokarnik, Rührtechnik, Theorie and Praxis, Springer Verlag 1999). For the sake of completeness both processes will now be described using the definitions:

Dispersing:

Dispersing is a physical process by which a mixture of two or more components is made which is characterized by the components being insoluble and because the distribution of the dispersed material in the dispersion component is very fine, so that the dispersion appears as a homogenous, stable mixture. Dispersion is the generic term for all mixtures comprising a carrier medium containing a dispersed component.

Emulsifying:

Emulsifying is understood to be a particular dispersion process whereby the dispersion created is stable due to a low surface tension and the separated globules cannot be separated. Surface active substances are also frequently used to increase the stability of the emulsion produced. The surface active substances behave in this case as emulsifiers.

The differences between the patent and each of the previously published documents:

Regarding WO 99/26913 A1:

The method presented in WO 99/26913 A1 describes in principle a process working with static mixers. (Page 8, lines 16, 17). The static mixer comprises a pipe which is filled with balls or various other materials. (Page 8, lines 83 to 25). Other equipment or materials are given on page 9, which clearly replace or support the static mixer. An emulsifier is usually understood to be a chemical and not a piece of equipment. "Emulsifiers are supporting chemicals, with the help of which two insoluble liquids (e.g. water in oil) can be made into a stable, homogeneous mass called and emulsion. There are artificially and naturally occurring emulsifiers. Their molecule contains a water soluble (hydrophilic) and a fat soluble (lipophilic) region. This molecular structure has the ability to enter into an interchange with water and oil and to enable a microscopically tiny distribution of the water. For the emulsion margarine emulsifiers largely based on monoglycerides and diglycerides from vegetable oils and fats along with vegetable lecithin." (Deutsches Margarineinstitut) [are used]. The Turbulator mentioned on page 9, line 12 is a piece of equipment originally used in heating systems and in plain language means "Turbulence Producer". Its construction is similar to a static mixer, however, materials are not mixed but instead the heat transfer to the pipe wall is improved (refer: A. Klaczak Heat and Mass Transfer Springer Publishers Heidelberg 1996).

Page 14, lines 10 to 13 repeat the fact that the reactor comprises a pipe filled with balls. The high pressure required for this process is referred to in lines 22 and 23. On page 16, lines 9 to 12, the so-called "Dynamic Emulsifier" is also described as a static mixer which in this case consists of a bent pipe. Page 16, line 30 repeats again that the process concerned is a high-pressure process.

From patent claims three, four, five, seven and eight of WO 99/26913 A1, it can be recognized that a type of static mixer has been described which has nothing to do with the invention under consideration. This is also easily recognized in diagrams FIG. 1 and FIG. 2.

For the sake of completeness, it is mentioned that under particularly favorable circumstances dispersions can also be produced using a static mixer. The problem with this is, however; that it is necessary for the shear stress to be maintained long enough. The problem present in this is, therefore, that an increase in the flow-rate increases the shear rate while simultaneously the residence time in the mixer is reduced. The globule size obtainable in a static mixer is, however, amongst other factors also a function of the residence time. This disadvantage of static mixers does not occur with dispersion equipment (refer: Marko Zlokamik, Riihrtechnik, Theorie and Praxis, Springer Verlag 1999).

The other points presented in WO 99/26913 A1 such as purification, washing, distillation, etc will not be dealt with here because they are processes which are well-known and widely used.

Regarding DE 199 08 978 A1:

In DE 199 08 978 A1, a process is described that performs the acid esterification and trans-esterification in one process step. Sulfuric acid is usually used as the catalyst for the acid esterification and potassium hydroxide or sodium hydroxide for the trans-esterification, because the different catalysts neutralize each other when mixed and the process must comprise at least two process steps. The document describes the simultaneous acid esterification and trans-esterification in one reaction step using sulfuric acid as the only catalyst. As far as the equipment arrangement is concerned, the process is to be treated as a cascade of a conventional "mixer-setter". As such DE 199 08 978 A1 does not present a similar example of the invention under consideration.

Figure 1:
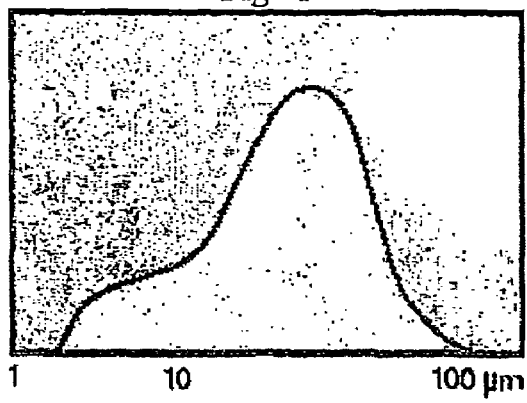
FIG. 1 to 5 show different globule size distributions.
Figure 2:
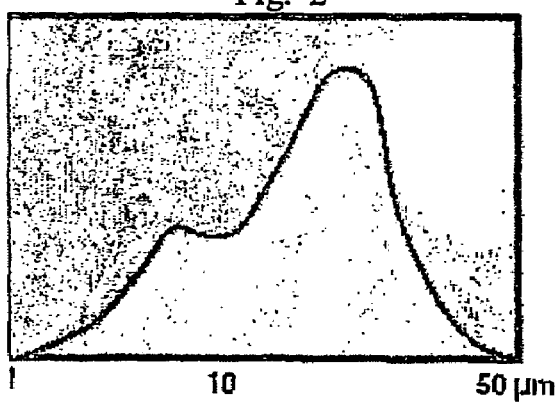

Regarding EP 0 249 463 A2:

With regard to this document it is to be noted that it essentially has nothing to do with the invented dispersion method. It describes a method for the pre-acid esterification and trans-esterification in two separate steps. A totally normal, frequently used mixing vessel is shown in FIG. 2. This type of mixing vessel is currently normally used for acid esterification and relates to the state of the technique. According to FIG. 1, it can be recognized that it concerns first of all the acid esterification, followed by trans-esterification. Here, EP 0 249 463 A2 differentiates itself fundamentally from DE 199 08 978 A1, which performs the acid esterification and trans-esterification in one step using the same catalyst. It is important to point out that the time references made in FIGS. 3 to 6 can be at least halved using the invented process. (This is also the case for the acid esterification which proceeds significantly slower than the trans-esterification). EP 0 249 463 A2 therefore describes a process corresponding to the state of the technique without demonstrating anything new.

Regarding U.S. Pat. No. 4,668,439 A:

U.S. Pat. No. 4,668,439 A differentiates itself from the invented process in several important points. Firstly, it concerns a process which works with gaseous methanol. The process occurs at high temperatures (230 to 240° C.) (Table 1, pages 9 and 10). As conducted according to Example 1 (Pages 7 and 8), the trans-esterification occurs in a very normal mixing container. In comparison to the dispersion process, a reaction time of 3.75 hours is given (page 7, line 57). As mentioned on page 11, point 7, the process occurs under pressure. Here it also differentiates itself from the dispersion process.

Regarding DE 196 38 460 A1:

DE 196 38 460 A1 concerns itself essentially not with the acid esterification and trans-esterification but with the most efficient separation possible of the glycerin phase from the ester produced. As described on page 4 line 45 to 63, this invention makes use of the fact that the ester is much more soluble than triglycerides or partial glycerides in near supercritical media. The production of esters using dispersion equipment can be found in neither the patent claims on pages 7 and 8 nor can it be seen in the drawing FIG. 1. The methods described in Example 3 and Example 4 using a solid catalyst to perform the trans-esterification are even diametrically opposed to the dispersion method. It is not possible to use a solid catalyst with the dispersion method.

The method used in Examples 1 and 2 is a common form of trans-esterification, however, here it is mainly used with reference to the separation of ester. The dispersion method can also be useful here for the production of ester. Extractive methods using supercritical media are most certainly common (decaffeinated coffee among others), however, currently not for the production of free fatty acid methyl ester.

Regarding DE 100 43 644 A1:

DE 100 43 644 A1 describes a process for the continuous production of biodiesel using so-called "micro reactors". These micro reactors, as they are drawn in FIG. 1, have nothing in common with the invented dispersion method. The differences are substantiated in that it clearly involves a process which works with a static mixer similar to WO 99/26913 A1. The process similarity between DE 100 43 644 A1 and WO 99/26913 A1 is significantly greater than between DE 100 43644 A1 and the invention. Further, it concerns a multi-step process (page 4, line 50) while the invention concerns a single step process.

As this argumentation shows, the documents presented have nothing to do with the current invention. It is clear that the acid esterification and trans-esterification are performed using the dispersion process. The advantages of the invented process are that the acid esterification and trans-esterification can be conducted each in one stage through the use of suitable equipment; the prevention of a stable dispersion can be achieved through the selection of suitable equipment; and that the phase separation is 90 percent complete in less than 30 minutes through the selection of suitable equipment. Through this process it becomes possible, in combination with suitable separation equipment (coalescence separator, separators, sloped plate clearers, etc.), that the separation can occur in situ.

On the basis of our own inquiries and on the basis of statements from the world's leading producer of dispersion equipment it can be said that the process has, to date, not been used anywhere. The reason for this is that the desired separation cannot take place as a result of incorrect equipment being selected. Hence the process is new.

When considering how to accelerate the acid esterification and trans-esterification reaction, consideration must be given to the fact that the reaction concerns a heterogenic chemical reaction. The reason for this is the fact that the two reactants (fats or oil or free fatty acids and methanol) are only soluble to a very limited extent in each other. In principle, heterogenic reactions are a combination of chemical reactions and mass transport phenomena, however, they are even more complicated for the following reasons:

Since the reacting compounds are present in two phases, the mass transfer to the phase boundary must be considered as transport in two opposing directions.

Hydrodynamic phenomena play a significantly more important role in these systems.

In most cases chemical and physical process steps take place simultaneously and cannot be analyzed separately.

The solubility of components in both phases must be considered because this determines whether the reaction takes place in just one or both phases.

One can apparently accelerate a heterogenic chemical reaction through improving the phase contact significantly. This was revealed even in our first experiment, where we mixed the usual reactants for the production of fat methyl ester and processed the components intensively using a dispersion machine instead of stirring with a propeller or other agitator typical in the chemical industry. The increased surface area for phase contact created by the intensive processing helped cause the acid esterification and transesterification reaction to proceed practically to competition in a very short time.

The invented process is characterized by the fact that the fats and oils present in liquid form and perhaps in mixtures with free fatty acids are mixed with commercially pure methyl alcohol in the presence of a basic or acidic catalyst so that the phase contact between both insoluble reactants (fat or oil or fatty acids and methanol) is increased by a suitable procedure, so that the acid esterification or trans-esterification reaction can proceed to completion in a very short time. The apparatus used is able to produce a dispersion with a globule size of about 1 µm.

The anticipated long separation time for the phases, due to the production of a dispersion, surprisingly did not occur. After just ten minutes of trans-esterification, the glycerin phase can be clearly seen, and the separation is already 90 percent complete.

The dispersion equipment must be able to create the desired globule size or globule size distribution by creating sufficient shear force.

The invention claimed is:

1. A method for esterifying a fatty acid, an oil, or a fat, the method comprising:
   introducing a liquid raw material to a dispersion machine, said liquid raw material selected from the group consisting of fatty acids, oils, fats, and combinations thereof, said liquid raw material further comprising a catalyst selected from the group consisting of an acid catalyst and a base catalyst; and
   dispersing a short chain alcohol in said liquid raw material to form a dispersion, said dispersion having a globule size between about 1 µm and 50 µm.

2. The method of claim 1, wherein said short chain alcohol is methyl alcohol.

3. The method of claim 1, wherein said short chain alcohol is selected from the group consisting of methyl alcohol, ethyl alcohol, propyl alcohol, butyl alcohol, pentyl alcohol, and combinations thereof.

4. The method of claim 1, wherein said dispersion machine comprises a multistage, high speed dispersion machine.

5. The method of claim 1, wherein said globule size is between about 5 μm and 15 μm.

6. The method of claim 1, wherein said globule size is between about 5 μm and 50 μm.

7. The method of claim 1, wherein said globule size is between about 1 μm and 15 μm.

8. A method for transesterifying a fatty acid, an oil, or a fat, the method comprising:

introducing a liquid raw material to a dispersion machine, said liquid raw material selected from the group consisting of fatty acids, oils, fats, and combinations thereof, said liquid raw material further comprising a catalyst selected from the group consisting of an acid catalyst and a base catalyst; and dispersing a short chain alcohol in said liquid raw material to form a dispersion, said dispersion having a globule size between about 1 μm and 50 μm.

9. The method of claim 8, wherein said short chain alcohol is methyl alcohol.

10. The method of claim 8, wherein said short chain alcohol is selected from the group consisting of methyl alcohol, ethyl alcohol, propyl alcohol, butyl alcohol, pentyl alcohol, and combinations thereof.

11. The method of claim 8, wherein said dispersion machine comprises a multistage, high speed dispersion machine.

12. The method of claim 8, wherein said globule size is between about 5 μm and 15 μm.

13. The method of claim 8, wherein said globule size is between about 5 μm and 50 μm.

14. The method of claim 8, wherein said globule size is between about 1 μm and 15 μm.

* * * * *